US006174538B1

(12) United States Patent
Branly et al.

(10) Patent No.: US 6,174,538 B1
(45) Date of Patent: *Jan. 16, 2001

(54) BAIT WITH CUCURBITACIN (75) Inventors: Keith L. Branly, Brandon, FL (US); James M. Gaggero, Citrus Heights, CA (US); Chel W. Lew, San Antonio, TX (US); Cathy S. Lamb, Westerville, OH (US)

(73) Assignee: Micro Flo Company, Memphis, TN (US)

( * ) Notice: Under 35 U.S.C. 154(b), the term of this patent shall be extended for 0 days.

This patent is subject to a terminal disclaimer.

(21) Appl. No.: 08/194,358

(22) Filed: Feb. 8, 1994

Related U.S. Application Data (63) Continuation-in-part of application No. 07/784,506, filed on Oct. 31, 1991, now Pat. No. 5,484,587.

(51) Int. Cl.$^7$ ................................................ A01N 25/10
(52) U.S. Cl. ........................ 424/408; 424/84; 424/405; 424/406; 424/418
(58) Field of Search ........................... 424/405, 406, 424/407, 418, 492, 499, 84, 410, 195.1, 408

(56) References Cited

U.S. PATENT DOCUMENTS

| | | | |
|---|---|---|---|
| 4,615,883 | * 10/1986 | Nelsen et al. | 424/84 |
| 4,764,272 | 8/1988 | Herrnstadt et al. | |
| 4,764,372 | * 8/1988 | Herrnstadt | 424/93 |
| 4,985,413 | * 1/1991 | Kohama et al. | 514/79 |
| 5,120,540 | 6/1992 | Doane et al. | 424/195.1 |

FOREIGN PATENT DOCUMENTS

| | | |
|---|---|---|
| 1195922 | 6/1983 | (CA) . |
| 1195922 | * 10/1985 | (CA) . |

| | | |
|---|---|---|
| 8504074 | * 9/1985 | (WO) . |

OTHER PUBLICATIONS

I. Aguinagalde, J.M. Ortiz, F. Rodriguez and C. Cedano, "Chemosystematic Survey of Cultivated *Cucurbita* Species," Journal of Horticultural Science, 65(6):649–655, (1990).

J.F. Andersen and R.L. Metcalf, "Identification To A Volatile Attractant For *Diabrotica and Acalymma* SPP. From Blossoms of *Cucubita maxima* Duchesne", Journal of Chemical Ecology, vol. 12, No. 3, pp. 687–699 (1986).

J.F. Andersen and R.L. Metcalf, Factors Influencing Distribution of *Diabrotica* SPP. In Blossoms of Cultivated *Cucurbita* SPP., Journal of Chemical Ecology, vol. 13, No. 4, pp. 681–699 (1987).

M. Arisawa, J.M. Pezzuto, A.D. Kinghorn, G.A. Cordell and N.R. Farnsworth, Plant Anticancer Agents XXX: Cucurbitacins from *Ipomopsis Aggregata* (Polemoniaceae), Journal of Pharmaceutical Sciences, vol. 73, No. 3, pp. 411–413 (1984).

Tom Arthur, "New Approach To Rootworm Control: Manipulating adult populations may one day greatly enhance corn rootworm control", Farm Chemicals, (Jul. 1989).

Mohamed A. Ba–Amer and W.P. Bemis, Fruit and Seed Development in *Cucurbita foetidissima*, pp. 297–299 (1968).

J.W. Berry, A.C. Gathman, J.M. Nelson, J.C. Scheerens, "Buffalo Group Research Status and Potential for Commercialization as a Cucurbitacin Source", (Apr. 1985).

(List continued on next page.)

*Primary Examiner*—Neil S. Levy
(74) *Attorney, Agent, or Firm*—Roylance, Abrams, Berdo & Goodman, L.L.P.

(57) ABSTRACT

Baits useful against diabroticine mature and immature beetles contain (a) an insecticide and (b) a feeding stimulant containing a cucurbitacin in a gelatin binder.

11 Claims, 3 Drawing Sheets

OTHER PUBLICATIONS

J.W. Berry, J.C. Scheerens and W.P. Bemis, "Buffalo Gourd Roots: Chemical Composition and Seasonal Changes in Starch Content", J. Agric. Food Chem., vol. 26, No. 2, pp. 354–356, (1978); "Cucurbit Root Starches: Isolationa nd Some Properties of Staches from *Cucurbita foetidissima* HBK and *Cucurbita digitala* Gray," J. Agric. Food Chem., vol. 23, No. 4, pp. 825–826 (1975).

M. Brusko, "He Tells EPA What To Do: Better systems, fewer products are the key to safer, more profitable farming, this farmer says", The New Farm Magazine, Nov./Dec., pp. 11–16, (1989).

S.J. Castle, T.M. Perring, C.A. Farrar and A.N. Kishaba, "Field and Laboratory Transmission of Watermelon Mosaic Virus 2 and Zucchini Yellow Mosaic Virus by Various Aphid Species", The American Phytopathological Society, vol. 82, No. 2, pp. 235–240, (1992).

J.T. Alves Costa and W.P. Bemis, "After–ripening effect on seed germination and viability of *Cucurbita foetidissima* seed", reprinted from *Turrialba*, vol. 22, No. 2, pp. 207–209, (1972).

N.J. Daghir, H.K. Mahmoud and A. El–Zein, "Buffalo Gourd (*Cucurbita foetidissima*) Meal: Nutritive Value and Detoxification", Nutrition Reports International, vol. 21, No. 6, pp. 836–847, (1980).

A. David, D.K. Vallance, "Letters to the Editor: Bitter Principles of Cucurbitaceae", Abstracts, pp. 295–297, (1955).

C.J. Deheer and D.W. Tallamy, "Affinity of Spotted Cucumber Beetle (Coleoptera: Chrysomelidae) Larvae to Cuburbitacins", Entomological Society of America, pp. 1173–1175, (1991).

J.C. Delouche, T.W. Still, M. Raspet and M. Lienhard, "The Tetrazolium Test For Seed Viability", Mississippi Agricultural Experiment Station Technical Bulletin, pp. 1–63, (1962).

M.L. Dreher, J.C. Scheerens, C.W. Weber and J.W. Berry, "Nutritional Evaluation of Buffalo Gourd Root Starch", Nutrition Reports International, vol. 23, No. 1, pp. 1–9, (Jan. 1981).

D.A. East, J.V. Edelson, E.L. Cox and M.K. Harris, Evaluation of screening methods and search for resistance in muskmelon, *Cucumis melo* L., to the two–spotted spider mite, *Tetranychus urticae* Koch, Crop Protection, vol. 11, pp. 39–44 (Feb. 1992).

P.R. Enslin, "Bitter Principles of the Cucurbitaceae I.—Observations on the Chemistry of Cucurbitacin A", J. Sci. Food Agric. 5, pp. 410–416, (Sep. 1954).

M.L. Dreher and J.W. Berry, "Buffalo Gourd Root Starch: Part I. Properties and Structure", Starch/Starke 35, Nr. 3, pp. 76–81 (1983).

M.L. Dreher, A.M. Tinsley, J.C. Scheerens and J.W. Berry, "Buffalo Gourd Root Starch: Part II. Rheologic Behavior, Freeze–thaw Stability and Suitability for Use in Food Products", Starch/Starke 35, Nr. 5, pp. 157–162 (1983).

J.E. Ferguson, D.C. Fischer and R.L. Metcalf, "A Report of Cucurbitacin Poisonings in Humans", CGC, 6:73–74, (1983).

J.E. Ferguson, R.L. Metcalf and D.C. Fischer, "Disposition and Fate of Cucurbitacin B in Five Species of Diabroticites", Journal of Chemical Ecology, vol. II, No. 9, pp. 1307–1321(1985).

J.E. Ferguson and R.L. Metcalf, "CUCURBITACINS Plant–Derived Defense Compounds for Diabroticites (Coleoptera: Chrysomelidae)", Journal of Chemical Ecology, vol. II, No. 3, pp. 311–319 (1985).

S. Gitter, R. Gallily, B. Shohat and D. Lavie, "Studies on the Antitumor Effect of Cucurbitacins", SBLI, pp. 516–521 (Oct. 1960).

J. Guha and S.P. Sen, "The Cucurbitacin—A Review", The Plan Biochemical Journal 2(1):12–28 (1975).

J.F. Harrington, "Effect of Fruit Maturity and Harvesting Methods on Germination of Muskmelon Seed", American Society for Horticultural Science, vol. 73, pp. 422–430, (Oct. 1958).

B.T. Hawthorne, "Effects of cultural practices on the incidence of storage rots in *Cucurbita* spp.", New Zealand Journal of Crop and Horticultural Science, vol. 17:49–54 (1989).

D. Hest, "Rootworms May Die for Love Potion No. 9", The Farmer, 103(13):27 (Aug. 1987).

A.D. Holmes, "Germination of Seeds Removed from Mature and Immature Butternut Squashes after Seven Months of Storage", American Society for Horticultural Science, V. 62, pp. 232–236 (1953).

W.L. Howe, J.R. Sanborn and A.M. Rhodes, "Western Corn Rootworm Adult and Spotted Cucumber Beetle Associations with *Cucurbita and Cucurbitacins*", Environmental Entomology, vol. 5, No. 6, pp. 1043–1048 (Dec. 1976).

H.E. Hummel and J.F. Anderson, "Secondary plant factors of Cucurbita species suppress sex attraction in the beetle Diabrotica under cimpunctata howardi", Proc. 5th int. Symp. Insect–Plant Relationshps, Wageningen, pp. 163–167 (1982).

T.F. Hutt and M.E. Herrington, "The Determination of Bitter Principles in Zucchinis", J. Sci. Food Agric. vol. 36, pp. 1107–1112 (1985).

P.J. Hylands and A.M. Salama, "Cucurbitacin S. A New Cucurbitacin From Bryonia Dioica", Phytochemistry, vol. 15, pp. 559–560 (1976).

P.J. Hylands and M.T. Oskoui, "3α–Hydroxy–Multiflora–7, 9(11)–Dien–29α–OIC Acid, A New Triterpene from Bryonia Dioica", Phytochemistry, vol. 18, pp. 1843–1845 (1979).

P.J. Hylands, E.S. Mansour, M.T. Oskoui, "Bryocoumaric Acid, a New Triterpene from Bryonia dioica", reprinted from Journal of The Chemical Society, pp. 2933–2936 (1980).

P.J. Hylands and E.S. Mansour, "New Cucurbitacin Derivatives from Bryonia dioica Jacq.", J. Chem. Soc. Perkin Trans. I, pp. 2821–2825 (1983).

J.C. Kirschmann and R.L. Suber, "Letter to the Editor: Recent Food Poisonings from Cucurbitacin in Traditionally Bred Squash", Fd Chem. Toxic, vol. 27, No. 8, pp. 555–556 (1989).

D.R. Lance and G.R. Sutter, "Field—Cage Tests of Semichemical – Based Toxic Baits for Diabrotica Bettles: Effects of Particle Distribution and Attractant Content", (Mar. 1990).

D.R. Lance and G.R. Sutter, "Field–Cage and Laboratory Evaluations of Semiochemical–Based Baits for Managing Western Corn Rootworm (Coleoptera: Chrysomelidae)", Journal of Economic Entomology, vol. 83, No. 3, pp. 1085–1090 (Jun. 1990).

D.R. Lance and G.R. Sutter, "Semichemical–based Toxic Baits for *Diabrotica virgifera virgifera* (Coleoptera: Chrysomelidae): Some Effects of Particle Distribution and Attractant Content", J. Econ. Entomol. Forage and Row Crops.

D.R. Lance and G.R. Sutter, "Field Tests of Semichemical–based Toxic Baits for Suppression of Corn Rootworm Beetles (Coleoptera; Chrysomeliadae)", J. Econ. Entomol. Forage and Row Crops, (Mar. 1991).

D.R. Lance and G.R. Sutter, "Semichemical–Based Toxic Baits for *Diabrotica virgifera virgifera* *Coleoptera: Chrysomelidae): Effects of Particle Size, Location, and Attractant Content", Journal of Economic Entomology, vol. 84, No. 6, pp. 1861–1868 (Dec. 1991).

J.R. Mason and T. Turpin, "Cucurbitacin–Adulterated Diet Is Avoided By Captive European Starlings", Cucurbitacins: J. Wildl. Manage 54:(4), pp. 672–676 (1990).

R. Mata, P. Castaneda, M.R. Camacho, "Chemical Studies on Mexican Plants Used In Traditional Medicine v. Cucurbitacin Glucosides From Cigarrilla, Mexicana", Journal of Natural Products, vol. 51, No. 5, pp. 836–839 (Sep.–Oct. 1988).

R. Mata, M.R. Camacho, E. Cervera, R. Bye and E. Linarea, "Secondary Metabolites From Hintonia Latiflora", Phytochemistry, vol. 29, No. 6, pp. 2037–2040 (1990).

Lance J. Meinke, "1985 Adult Western Corn Rootworm Suppression Study Large Scale Griffin Formulation Evaluation", paper for Department of Entomology, University of Nebraska, Lincoln, NE, pp. 1–4 (1985).

L.J. Meinke, Z.B. Mayo and T. J. Weissling, "Pheromone Delivery System: Western Corn Rootworm (Coleoptera: Chrysomelidae) Pheromone Encapsulations in a Starch Borate Matrix", Journal of Economic Entomology, vol. 82, No. 6, pp. (Dec. 1989).

R.L. Metcalf, R.A. Metcalf and A.M. Rhodes, "Cucurbitacins as kairomones for diabroticite beetles", Proc. Natl. Acad. Sci. USA, vol. 77, No. 7, pp. 3769–3772 (Jul. 1980).

R.L. Metcalf, A.M. Rhodes, R.A. Metcalf, J. Ferguson, E.R. Metcalf and P. Lu, "Cucurbitacin Contents and Diabroticite (Coleoptera: Chrysomelidae) Feeding upon *Cucurbita spp.*", Etomological Society of America, vol. 11, No. 4, pp. 931–937 (Aug. 1982).

R.L. Metcalf, J.E. Ferguson, D. Fischer, R. Lampmann and J. Anderson, "Controlling Cucumber Beetles and Corn Rootworm Beetles with Baits of Bitter Cucurbit Fruits and Root", CGC 6:79–81 (1983).

Robert L. Metcalf, "Coevoluntionary Adaptations of Rootworm Beetles (Coleoptera: Chrysomelidae) to Cucurbitacins", Journal of Chemical Ecology, vol. 12, No. 5, (1986).

R.L. Metcalf, J.E. Ferguson, R. Lampman and J.F. Anderson, "Dry Cucurbitacin–containing Baits for Controlling Diabroticite Beetles (Coleoptera: Chrysomelidae)", Journal of Economic Entomology, vol. 80, No. 4, pp. 870–874 (Aug. 1987).

R.L. Metcalf and R.L. Lampman, "The Chemical Ecology of Diabroticites and Cucurbitaceae", Experientia 45, pp. 240–247 (1989).

Daniel E. Moerman, "Medicinal Plants of Native America", University of Michigan Museum of Anthropology Technical Reports, No. 19, (1986).

C.A. Mullin, Ali A. Alfatafta, J.L. Harman, S.L. Everett and A.A. Serino, "Feeding and Toxic Effects of Floral Sesquiterpene Lactones, Diterpenes, and Phenolics from Sunflower (*Helianthus annuss L.*) on Western Corn Rootworm", Journal of Agricultural and Food Chemistry, vol. 39, No. 12, pp. 2293–2299 (1991).

Gary Nabhan and Jill Thompson, "Wild Cucurbita in Arid America: Ethnic Uses, Chemistry and Geography", Native Seeds/SEARCH, pp. 1–20 (1985).

J.M. Nelson, J.C. Scheerens, J.W. Berry and W.P. Bemis, "Effect of Plant Population and Planting Date on Root and Starch Production of Buffalo Gourd Grown as an Annual", J. Amer. Soc. Hort. Sci. 108(2):198–201 (Mar. 1983).

J.M. Nelson, J.C. Scheerens, T.L. McGriff and A.C. Gathman, "Irrigation and Plant Spacing Effects on Seed Production of Buffalo and Coyote Gourds", Agronomy Journal, vol. 80, No. 1, pp. 60–65 (1988).

J.M. Nelson, J.C. Scheerens, D.A. Bucks and J.W. Berry, "Irrigation Effects on Water Use, and Production of Tap Roots and Starch of Buffalo Gourd", Agronomy Journal, vol. 81, No. 3, pp. 439–442 (1989).

John Nelson, "The Buffalo Gourd—Information on its Culture for Root and Seed Production", paper for University of Arizona, Maricopa Agricultural Center, pp. 1–6 (Jan. 1991).

R. Nishida and H. Fukami, "Sequestration of Distasteful Compounds By Some Pharmacophagous Insects", Journal of Chemical Ecology, vol. 16, No. 1, pp. 151–164 (199).

Jane Paul, "Getting Tricky With Rootworms: Here's a twist on the old bait–and–switch game", Agrichemical Age, pp. 6, 25E, and 30 (Mar. 1989).

T.M. Perring, C.A. Farrar, K. Mayberry and M.J. Blua, "Research Reveals Pattern of Cucurbit Virus Spread", Cailfornia Agriculture, vol. 46, No. 2, pp. 35–40 (Apr.–Mar. 1992).

M. Pitrat, "Linkage Groups in *Cucumis melo L.*", Journal of Heredity, 82:406–411 (1991).

D.R. Raemisch and F.T. Turpin, "Field Tests For An Adult Western Corn Rootworm Aggregation Pheromone Associated with the Phagostimulatory Characteristic of Bitter *Cucurbita spp.*", J. Agric. Entomol. 1(4):339–344 (Oct. 1984).

S. Rehm, P.R. Enslin, A.D.J. Mecuse and R.H. Wessels, "Bitter Principles of the Cucurbitaceae. VII—The Distribution of Bitter Principles in this Plant Family", J. Sci. Food Agric., pp. 679–686 (Dec. 1957).

A.M. Rhodes, R.L. Metcalf and E.R. Metcalf, "Diabroticite Beetle Responses to Cucurbitacin Kairomones in *Cucurbita* Hybrids", J. Amer. Soc. Hort. Sci. 105(6):838–842 (1980).

K.S. Rymal, O.L. Chambliss, M.D. Bond and D.A. Smith, "Squash Containing Toxic Cucurbitacin Compounds Occurring in California and Alabama", Journal of Food Protection, vol. 47, pp. 270–271 (Apr. 1984).

S.M. Sakr and E.E. Mahmoud, "Viability of Seeds Harvested from Fruits at Different Stages of Maturity", American Society for Horticultural Science, pp. 326–329 (1952).

J.C. Scheerens and J.W. Berry, "Buffalo Gourd: Composition and Functionality of Potential Food Ingredients", Cereal Foods World, vol. 31, No. 2, pp. 183–192 (Feb. 1986).

G.C. Sharma and C.V. Hall, "Influence of Cucurbitacins, Sugars, and Fatty Acids on Cucurbit Susceptibility to Spotted Cucumber Beetle", J. Amer. Soc. Hort. Sci. 96(5):675–680 (1971).

G.S. Stoewsand, A. Jaworski, S. Shannon and R.W. Robinson, "Toxicologic Response in Mice Fed Cucurbita Fruit", Journal of Food Protection, vol. 48, No. 1, pp. 50–51 (Jan. 1985).

H. Stuppner and H. Wagner, "New Cucurbitiacin Glycosides from *Picrorhiza kurrooz*", Planta Medica 55, pp. 559–563 (1989).

G.R. Sutter and D.R. Lance, "New Strategies for Reducing Insectcide Use in the Corn Belt", Sustainable Agriculture Field Research and Education, pp. 231–249 (1991).

Weissling et al., "Effect of Starch–based Corn Rootworm Baits on Selected Nontarget Insect Species: Influence of Semiochemical Composition", *J. Econ. Entomol.*, 84 (4), 1235–1241 (Aug. 1991).

Weissling et al., "Effect of Starch–based Corn Rootworm Baits on Selected Nontarget Insect Species: Influence of Semiochemical Composition", abstract presented at the Entomological Society of America North Central Branch Meeting, (Mar. 1990).

Levine et al., "Control of Western Corn Rootworms with Semiochemical Baits in Illinois", abstract presented at Entomological Society of America North Central Branch Meeting, (Mar. 1990).

Trimnell et al. "Pesticide Encapsulation Using a Starch–Borate Complex as Wall Material", *J. Appl. Poly. Sci.,* vol. 27, 3919–3928 (1982).

Dunkle et al., "Starch–Encapsulated *Bacillus thuringiensis:* A Potential New Method for Increasing Environmental Stability of Entomopathogens", *Environ. Entom.,* vol. 17, No. 1, 120–126 (1988).

Tollefson, "Treatment of Adult Corn Rootworms with a Semiochemical and Insecticide Mixture to Disrupt Oviposition and Subsequent Larval Damage" (1984).

Tollefson, "Control of Western Corn Rootworm Larvae Through Adult Suppression" (1988).

Corn Insects Project, "Field Cage and Laboratory Evaluation of Semiochemical–based Baits", *Report to NCR–46 Corn Rootworm Technical Committee,* Minneapolis, Minnesota Jan. 24 & 25, 1989.

Weissling et al., "Summary of 1988 Experiments with Starch Encapsulated Semiochemicals and Insecticides", *Report to NCR—46 Corn Rootworm Technical Committee,* Minneapolis, Minnesota Jan. 24 & 25, 1989.

Corn Insects Project, "Limited Field Trials of Semiochemical–based Bait for Control of Adult Northern and Western Corn Rootworms", presentation to NCR–46 Corn Rootworm Technical Committee, Indianapolis, Indiana, Jan. 16–17, 1990.

Corn Insects Project, "Effects of Particle Size, Distribution, and Attractant Content on Efficacy of Semiochemical–based Baits in Walk–in Field Cages", presentation to NCR–46 Corn Rootworm Technical Committee, Grand Rapids, Michigan Jan. 16–17, 1990.

Douglas W. Tallamy, "Squash Beetle Feeding Behavior: An Adaptation Against Induced Cucurbit Defenses", Ecology, 66(5) pp. 1574–1579 (Oct. 1985).

D.W. Tallamy and V.A. Krischik, "Variation and Function of Cucurbitacins in *Cucurbita:* An Examination of Current Hypotheses", The American Naturalist, vol. 133, No. 6, pp. 766–786 (Jun. 1989).

D.W. Tallamy and E.S. McCloud, "Squash Beetles, Cucumber Beetles, and Inducible Cucurbit Responses", Phytochemical Induction By Herbiores, pp. 155–181 (1991).

T.J. Weissling and L.J. Meinke, "Potential of Starch Encapsulated Semiochemical/Insecticide Formulations for Adult Corn Rootworm (Coleoptera: Chrysomelidae) Control", Journal of Economic Entomology, Forage and Row Crops, pp. 1–36 (87/89).

T.J. Weissling, "Behavioral Responses of *Diabrotica* Adults to Plant–Derived Semichemicals Encapsulated in a Starch Borate Matrix", Entomol. Exper. Appl. vol. 1, 53:219–228 (Aug. 1990).

T.J. Weissling, L.J. Meinke, D. Trumnell and K.L. Golden, Behavioral Responses of *Diabrotica* Adults to Plant–Derived Semiochemicals Encapsulated in a Starch Borate Matrix, Entomol. Exp. Appl 53:219–228 (1989).

T.J. Weissling and L.J. Meinke, "Potential of Starch Encapsulated Semiochemical–Insecticide Formulations for Adult Corn Rootworm (Coleoptera: Chrysomelidae) Control", Entomological Society of America, vol. 84, No. 2, pp. 601–609 (Jul. 1991).

T.J. Weissling, L. J. Meinke and K.A. Lytle, "Effect of Starch–Based Corn Rootworm (Coleoptera: Chrysomelidae) Baits on Selected Nontarget Insect Species: Influence of Semiochemical Composition", Entomological Society of America, vol. 84, No. 4, pp. 1235–1241 (Aug. 1991).

T.J. Weissling and L.J. Meinke, "Semiochemical—Insecticide Bait Placement and Vertical Distribution of Corn Rootworm (Coleoptera: Chrysomeliadae) Adults: Implications for Management", Entomological Society of America, vol. 20, No. 3, pp. 945–952 (Jun. 1991).

Robert E. Young, "The Effect of Maturity and Storage on Germination of Butternut Squash Seed", American Society For Horticultural Science, vol. 53, pp. 345–347 (1949).

P. Yang, S. Liu, Z. Coa, W. Chang and C. Che, "Cucurbitacin Contents in *Hemsleya dolichocarpa,*" American Journal of Chinese Medicine, vol. XIX, No. 1, pp. 51–56 (1991).

\* cited by examiner

BAIT WITH CUCURBITACIN

This is a continuation-in-part of copending application Ser. No. 07/784,506, filed on Oct. 31, 1991, now U.S. Pat. No. 5,484,587, the disclosure of which is incorporated herein by reference.

FIELD OF THE INVENTION

The invention relates to a bait having a particularly effective form and structure for control of various insects and particularly for immature and adult diabroticine beetles.

BACKGROUND OF THE TECHNOLOGY

Diabroticine beetles are a significant problem during the growth of, inter alia, corn (field, pop, seed, and sweet), beans, Cucurbitaceae (including cucumbers, melons, squash, and pumpkins), peanuts, peas, potatoes, and sweet potatoes. Corn is conveniently used to describe the effects of diabroticine beetles. These pests are the direct or indirect (i.e., as a vector for bacteria and inoculation of melons and squash) cause of millions of dollars of crop and garden damage annually. Damage by these beetles has continued despite over 30 years of attempts at control.

Diabroticine beetles encompass multivoltine and univoltine species. Multivoltine species (e.g., the southern corn rootworm) can produce up to 3 generations a year. Univoltine species (e.g., northern and western corn rootworm) have a life cycle that starts with eggs laid 4–24 inches below the soil surface in the Fall. In early Spring and over the course of several weeks, the larvae (a form of immature beetle) hatch and begin to feed on nearby roots thereby destroying the root's anchoring abilities and the microhairs responsible for mineral, nutrients, and water assimilation. If the plant roots have not been so damaged that the plants falls over, the yield from the affected plants is reduced due to impaired nutrition.

After feeding, the diabroticine larvae pupate and emerge from the ground as adult beetles. Univoltine beetles emerge at some time during mid July through August (depending on local climate). Male diabroticine beetles emerge about 1 week before the females (week 1) which, in turn, emerge at about the same time as corn silks emerge. Because the fresh silks emit a number of volatile agents which are attractive to both the male and female beetles, the 7–10 days of silking represents a period of high feeding activity for the beetles. The beetles immediately begin to migrate up the stalk toward the leaves, ears, and silks. This compulsion is quite strong since there is evidence that the beetles will not move down the corn stalk in response to attractants. Throughout this period, the beetles feed and mate.

The key to control of the diabroticine beetles is to disrupt the life cycle by affecting the immature and/or adult beetles. One method known in the art as "banding" refers to the practice of trying to control the larvae by applying a contact insecticide in or along a furrow containing planted seeds. The theory behind banding is that larvae will enter the treated area when searching for roots and die due to contact with the insecticide.

Unfortunately, microbial attack impairs the efficacy of insecticides in the soil well before all the larvae have had time to hatch and enter the treated band. Concerns for groundwater contamination, the impact on nontarget organisms (e.g., bird kill), and the hazards of human exposure to the toxic insecticides all restrict the use of soil insecticides that might be capable of surviving in the soil through the larval feeding stage.

The effectiveness of banding is also limited by the plants themselves. Plant roots often extend well beyond the treated band leaving the roots vulnerable to attack.

It has been proposed to use the tissue of dried gourds from the Cucurbitale order in combination with 0.01–10% by weight (wt %) of an insecticide to make a lethal bait for the control of diabroticine beetles. Due to genetic evolution, corn rootworm larvae have evolved to compulsively feed on cucurbitacins.

From Canadian Patent No. 1,195,922, the bitter tasting cucurbitacins in the gourd tissue acts as a compulsive feeding stimulant for diabroticine beetles but is a feeding deterrent to beneficial insects. By coating the gourd tissues with an insecticide according to the teachings of the disclosure, it was asserted that the beetles would compulsively consume a lethal quantity of insecticide.

It would be desirable to have a bait formulation that would provide a high level of efficacy against immature and mature diabroticine beetles when applied through conventional application equipment as a sprayable aqueous solution, as well as when applied as a dry granular bait.

SUMMARY OF THE INVENTION

It is an objective of the invention to provide a bait and method of use thereof having high levels of pest control and which is particularly effective against diabroticine populations.

It is another objective of the invention to provide a composition containing an intimate admixture of a feeding stimulant and insecticide in a form useful for application as a dry granular solid or as a solid suspended in aqueous solution using conventional application equipment.

In accordance with these and other objectives that will become apparent from the description herein, baits according to the invention comprise particulate composite baits comprising a binding agent comprising gelatin in which is homogeneously dispersed a mixture of (a) 0.01–99 wt % of diabroticidal insecticide; and (b) 0.01–99 wt % of a feeding stimulant comprising a cucurbitacin.

The present bait provides a physical form with high efficacy. The homogeneous distribution assures that consumption of cucurbitacin will also include consumption of insecticide by target insects until a lethal dose is achieved, while simultaneously serving as a feeding deterrent to nontarget insects and animals due to the bitter taste of the cucurbitacins. The bait exhibits a high rate of kill in targeted immature as well as mature diabroticine beetles at low material application rates.

DETAILED DESCRIPTION

The present invention provides cucurbitacin as a diabroticine feeding stimulant homogeneously dispersed with an insecticide in a binder matrix containing gelatin. Depending on the diameter of the bait, the bait can be applied in the form of a dry granular or an aqueous bait suspension applied through conventional spraying equipment.

1. Cucurbitacin Feeding Stimulant Component

The cucurbitacins useful in the present invention as feeding stimulants are well described in Canadian Patent No. 1,195,922, U.S. Pat. No. 4,880,624, and *The Merck Index*, 10th ed., p. 2609 (1983). Briefly summarized, plants in the cucurbitaceae order contain small quantities of oxygenated tetracyclic triterpenoid compounds (usually referred to as the cucurbitacins) that are responsible for the bitter taste of the plant tissue. Seventeen of the cucurbitacins have been isolated and identified by letters, namely cucurbitacins A, B, C, D, E, F, G, H, I, J, K, L, O, P, Q, R, in aglycone (somewhat water soluble) or glycoside (very water soluble) forms. The cucurbitacins B, D, E, I aglycone or glycoside forms thereof are preferred feeding stimulants for baits of the present invention.

The cucurbitacin can be added to the bait as a dilute cucurbitacin-containing solid or liquid with a concentration of less than about 0.01 wt % cucurbitacin, as a purified compound, or as a concentrated liquid containing more than about 0.01 wt %, preferably more than about 0.05 wt %, and even more preferably within the range of 0.05–0.5 wt % cucurbitacins. The cucurbitacins can be added as discrete particles homogeneously distributed throughout the bait or as a liquid stream that is homogeneously distributed throughout the bait. The cucurbitacin-containing material are preferably added as a discrete plant tissue particles which contain cucurbitacins, cucurbitacin-containing liquids applied to solid carriers such as a corn cob grit, or introduced as a concentrated liquid that is mixed homogeneously into the matrix with the process liquid used to spray dry the baits. Particularly preferred forms for introducing a cucurbitacin feeding stimulant component are dried powders of dried plant tissues or as a concentrated cucurbitacin solution containing 20–50 wt % solids and about 0.1–0.5 wt % cucurbitacins.

Plant tissues containing the highest levels of cucurbitacins include the roots of the buffalo gourd (*Cucurbita foetidissima*) which, when dried, contain about 0.3 % by weight cucurbitacins and fruits of cucurbitacin containing fruits. See, Metcalf Canadian Patent No. 1,195,922 for a list of cucurbitacin-rich plant species useful as cucurbitacin sources for the present invention. Other cucurbitan-containing materials useful for the invention may come from, inter alia, *C. andreana* NAUD, *C. cylindrata* Wats, *C. ecuadorensis* Cutl. and Whit., *C. foetidissima* HBK, *C. gracilior* Bailey, *C. lundelliana* Bailey, *C. martinezii* Bailey, *C. okeechobensis* Bailey, *C. palmata* Wats., *C. palmeri* Bailey, *C. pedatifolia* Bailey, *C. sororia* Bailey, and *C. texana* Gray.

Buffalo gourd root powder is a preferred source of solid cucurbitacin-containing material for use as the feeding stimulant component in baits of the invention because the root powder contains a significant quantity of starch. This starch acts as a sticking agent when wetted to assist the applied bait particles in adhering to the plant surface. Such adhesion properties are advantageous when bait particles are aerially applied. If desired, however, starch (e.g., food starch) may be added to enhance the sticking effects whether cucurbitacin-containing plant tissues are used or some other form of cucurbitacin.

The use of cucurbitacin-containing plant tissues has a number of practical benefits. First, the inherent chemical composition of cucurbitacin-containing plant tissue is responsible for the compulsive feeding effects. Cucurbitacin-containing plant tissues can, therefore, be used in a dry form which reduces the special handling and storage concerns with grinding, formulating, and storing moist plant tissues. Moreover, the stimulation effects are found at such extremely low levels that there are no special handling procedures for handling the cucurbitacin which is quite toxic in its pure form. Only the insecticides might require special handling.

References herein the "cucurbitacin-containing" shall mean plant tissue solids and either solid or liquid carriers containing at least one of the cucurbitacins A, B, C, D, E, F, G, H, I, J, K, L, O, P, Q, R aglycone or glycoside forms of any of these.

2. Insecticide Component

Insecticides useful for the invention are those effective to control the insect populations by killing or sterilizing the immature or adult beetles. Generally, an amount within the range of 0.01–99 wt %, preferably 0.1–50 wt %, even more preferably an amount within the range of 0.01–25 wt %. A particularly preferred amount of insecticide is within the range from about 5–25 wt % based on the total weight of the bait.

Insecticides useful in the invention are materials and biological agents that control diabroticine populations through lethal ingestion, sterilization, or other interference with the diabroticine life cycle. Exemplary insecticides include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, and phosmet); compounds which break down the beetle's digestive tract tissue including fluorine compounds (cryolite), zinc, and mercury; nicotine; rotenone; neem oil or azadiractin; natural or synthetic pyrethrins; petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); and microbials (e.g., Bacillus thuringiensis and entomopathic viruses such as diabroticidal viruses such as the bacculo viruses).

Most insecticides are commercially available in the form of a solid particle. Liquids may be used in the baits homogeneously mixed with the binder. The use of microencapsulated liquids or fine solids that become intimately bound are preferred for handling and control. In general, organophosphates and the carbamates are preferred with phorate, carbaryl and methomyl being most preferred.

Baits of the invention exhibit a surprisingly high level of diabroticine control while enabling the application of overall lower levels of insecticide relative to conventional practice. For example, the current EPA label application rate for control of diabroticine beetles by carbaryl is 454–908 grams active ingredient (AI) carbaryl per acre of treated area. With the present invention, however, the higher levels of control are realized by a significantly lower application rate. For carbaryl, this rate is within the range from about 2 to about 200 g AI/acre, preferably about 5–100 g AI/acre, and most preferably about 20–50 g AI/acre. Practical carbaryl formulations will translate into an application rate of 2–20 lbs. of bait per acre when formed as a dry granule using an inert carrier (such as corn cob grit or clay) or 5–50 ounces of bait applied from aqueous solution per acre.

The quantities of diabroticidal insecticides other than carbaryl are used in quantities proportional to their diabroticidal efficacy relative to the levels of carbaryl used herein.

As an example, diabroticidal insecticides that are 50% as effective as carbaryl are used in quantities of 5–400 g AI/acre, but insecticides that are twice as effective are used in quantities within the range from about 1–100 g AI/acre. The precise application rate of any particular insecticide when supplied in baits of the present invention is readily determinable by one in this art with the exercise of no more than the existing skill level after consideration of the present disclosure.

3. Gelatin Binder Component and Bait Forms

Binders for the present bait include gelatin and any additive materials in amounts thereof that are: (a) palatable to target insects; and (b) able to bind together the insecticide and cucurbitacin components yet (c) pass through extruders, sprayers, and agglomeraters conventionally used to form particles. Gelatin binders provide a source of hydratable solids which, in a sprayed bait or after moisture contacts a dry granule, cause the bait to exhibit a gumdrop-like, chewable consistency for an extended period of time that is highly palatable to target insects. Importantly, the gelatin binder will hydrate and soften without dissolving significantly or releasing the intimately admixed feeding stimulant and insecticide despite the application of the type of shear forces found in commercial spraying apparatus. The gelatin also exhibits good wetting and suspension in spray tanks.

Gelatin binders useful for the invention are hot water soluble, high bloom pork or beef gelatin. Because the tank mixing temperatures and field conditions where baits of the invention would be used are generally at temperatures much less than the solubility temperature of high bloom gelatins, the hot water solubility of these materials does not adversely affect use of the baits. Gelatins having a bloom strength within the range from about 200–300, more preferably within the range of about 275–300, are particularly preferred and exhibit a solubility in such cold water of less than about 5% by weight, preferably less than about 2 wt %, and most preferably less than about 1 wt %.

The binder of the bait is used in an amount within the range from about 1 wt % to about 95 wt % in a quantity sufficient to bind together the insecticide and cucurbitacin components in a structurally sound bait. Preferably, the binder is used in an amount of about 1 wt % to about 50 wt % and more preferably within the range from about 1–35 wt % based on the total weight of the bait. A particularly preferred amount of gelatin as the binder is within the range from about 5–30 wt % based on the total bait weight.

For sprayed baits, the binder should have a low solubility in cold water to ensure that the bait components are not released in the spray tank or cause undesired drift after passing through the spray nozzle. Generally, the binder for a sprayed bait should exhibit a solubility in cold water that is less than about 5 % by weight, preferably less than about 2 wt %, and most preferably less than about 1 wt %.

If intended for application through conventional spraying equipment, the baits are desirably formed into a roughly spherical bait having a diameter of less than about 1000 µm. Preferably, 100% of the bait exhibits a particle size within the range from about 100 µm to about 600 µm. Particularly effective particle sizes are when 100% of the bait particles are within the range of about 300 µm to about 600 µm. For homogeneously formed particles within these ranges, consumption of the feeding stimulant will necessarily involve consumption of the insecticide.

Dry granular baits, on the other hand, will generally exhibit a larger corresponding size within the range from about 800 µm to about 2000 µm. Within the range of about 600–800 µm, the baits can be used as either a sprayable bait or a dry granular bait depending on the cold water solubility of the binder employed.

Dry granular baits are desirably made by depositing a homogeneous mixture of cucurbitacin, insecticide, and binder on corn cob grit. One method for applying dry bait particles that has proven to be acceptable is to load dry corn cob grit having a size of 40–60 mesh (250–360 µm) with spray dried microsphere bait particles according to the invention. These corn cob particles have an open network of pores that will readily hold fine bait particles such as those of the invention yet present a sufficiently large particle size that the grit particles can be applied aerially without experiencing significant amounts of lost material due to bouncing off the plant surfaces upon landing. Preferably, porous carriers for the present bait particles have a bulk density of about that of corn cob grit. In practice, it has been found that the diabroticine beetles will consume bait particles from within the openings of the grit or those that have fallen out as a result of landing on the plant surface. Either mode of consumption results in a high rate of kill.

Alternatively, a plurality of <600 µm preformed baits, such as those dispersed by spraying, can be deposited on a grit carrier and held thereon with the same binder as in the bait or a different binder.

4. Additional Additives

A number of additional materials can be included in the baits of the present invention. Plasticizers can be used to enhance the softness of the hydrated bait and wetting in aqueous suspensions. Useful plasticizers include sorbitol, maltodextrin, glycerin, and sucrose in an amount within the range from about 5 wt % to about 20 wt %. Preferably, plasticizer is used in an amount within the range of about 1–10 wt %.

A preservative can be added in an amount sufficient to inhibit or prevent deterioration during storage and transport. Suitable preservatives include a material commercially available under the trademark Proxell and sodium benzoate. Suitable amounts of preservatives are within the range from about 0.05 wt % to about 1 wt %, preferably in an amount within the range of about 0.05–0.4 wt %.

Gums are useful in the binder for increasing palatability of the bait to the immature and adult beetles and, when the bait is to be distributed by spraying, as a hydratable solid in addition to gelatin that will swell and maintain a binding effect without dissolving in an aqueous spray medium. Suitable gums for the invention include xanthan gum, carrageenan, and gellan in an amount within the range of 0–10 wt %, preferably, within the range from about 0.01–5 wt %.

Clays can be used to increase the density of the bait particle when bait according to the invention is formed as a dry granular bait that is distributed without spraying. Clay is added to form a bulk bait density within the range of about 25 to about 50 lb/ft$^3$ (400–800 kg/m$^3$), preferably within the range of about 30–40 lb/ft$^3$ (480–640 kg/m$^3$), and even more preferably about 35 lb/ft$^3$ (560 kg/m$^3$). Clays useful in the invention include kaolin, montmorrilonite, attapulgite, and bentonite. Generally, such clays are used as a bait component in an amount within the range from about 1 wt % to about 30 wt %, preferably, about 5 wt % to about 20 wt %.

Silica can be used in the bait as a binder component to modify extrusion flow characteristics, methods of bait formation, and to alter the density of the final bait. Many forms of silica can be used, but fumed silica having a particle size of less than about 5 microns is preferred. Silica can be used in an amount within the range from about 5–30 wt %, preferably within the range from about 20–30 wt %.

The baits may also contain one or more attractants for the target insect. Attractants such as those in U.S. Pat. No. 4,880,624 are preferred for diabroticine insects.

The baits may also contain one or more additional feeding stimulants for the target insects. One supplementary stimulant useful with diabroticine insects is milled corn germ containing less than about 25 wt % of corn endosperm associated therewith.

The present bait can be made by forming a homogeneous mixture of finely divided particles of insecticide and cucurbitacin-containing material by many methods such as spray drying, prilling, centrifugal disk, extrusion, agglomeration, or by jet impact between two opposing nozzles. In forming the baits by such method, the individual insecticide particles and cucurbitacin-containing material (if used in a solid) are conveniently less than about 50 $\mu$m in diameter with sizes of less than about 25 $\mu$m being preferred.

5. Insects Controlled By the Present Baits

The present invention provides a method of using the baits to control insect infestations in a variety of plants. It should be noted that the term "insect" is used herein to denote the control of either immature or adult stages or both immature and adult stages so long as either form consumes solid food for sustenance and growth. In some multivoltine insect species exhibiting overlapping generations, application of the present baits can be used to control both adults and immature forms thereof simultaneously.

Insects that can be controlled with the present invention include insects of the diabroticine genus as well as cutworms, wireworms, billbugs, seed corn maggots, grubs, lesser corn stalk borer, seed corn beetle, flea beetles, European and Southwestern corn borer, fire ants and other ant species, onion maggots, sweet potato weevils, root maggots, and other types of chewing insects that feed on a variety of plants and whose feeding is stimulated by cucurbitacins.

Specific diabroticine insects that are advantageously controlled in accordance with the invention include the banded cucumber beetle (*Diabrotica balteata*), the green maize beetle (*Diabrotica decolor*), the twelve-spotted cucumber beetle (*Diabrotica duodecimpunctata*), the northern corn rootworm (*Diabrotica barberi*), the southern corn rootworm or spotted cucumber beetle (*Diabrotica undecimpunctata howardi*), the western spotted cucumber beetle (*Diabrotica undecimpunctata undecimpunctata*), the western corn rootworm (*Diabrotica virgifera virgifera*), the striped cucumber beetle (*Acalymma vittata*), Western striped cucumber beetle (*Acalymma trivittata*), the Mexican corn rootworm (*Diabrotica virgifera zeae*), *Diabrotica adelpha, D. speciosa speciosa, D. speciosa vigens, D. viridula, D. cristata, D. undecimpunctata sensulato, D. undecimpunctata tenella,* and *D. undecimpunctata duodecimnotata*.

A simple feeding test under controlled conditions is used to determine whether any designated insect will feed on cucurbitacin-containing baits. For example, dried buffalo gourd root powder can be deposited in a petri dish into which are introduced a limited number of test insects. Feeding stimulation is exhibited by insects clustering around powder clumps.

6. Population Control with Baits

When used as adulticides on diabroticine insects, bait particles of the present invention are applied to the plant surfaces just before emergence of the adult diabroticine beetles or when monitoring counts indicate an economic level of infestation. For corn, an economic infestation level for treatment is about 0.5–1 beetles per plant at prevailing crop values and treatment costs. If an economic level of infestation is not seen, commercial fields are not considered to be economically justified for treatment because the losses sustained by beetle damage are worth less than the cost of an average treatment.

Plants that can be protected according to the present invention include virtually any plant affected by diabroticine beetles. Examples of such plants include, inter alia, corn (field, pop, seed, and sweet), beans, Cucurbitaceae (including cucumbers, melons, squash, and pumpkins), peanuts, peas, potatoes, and sweet potatoes.

An example of treating corn serves as a convenient tool for illustrating the invention. At 7–10 days after first emergence of the adult beetles in corn, the beetle population will be at its peak. Baits of the present invention should on the plants by this time and remain effective for 1–3 weeks to cover overlapping beetle emergence and migration periods. This timing and duration maximize the control over beetles that will produce the progeny causing the succeeding year's root damage.

Dry particles or a liquid suspension of the bait particles are distributed over the tops of the plants to be treated by conventional ground or aerial spraying and equivalent methods with or without herbicides and/or plant nutrients that do not adversely affect the activity of the bait. The objective of such application methods is to deposit bait particles on the upper surfaces of the plant where the diabroticine beetles will locate them while foraging for food.

When used as a larvacide for diabroticine insects at planting, baits are applied to the soil in a furrow containing plant seeds or along at least one of the sides of the seed-containing furrow. Similarly, the baits can be applied post-emergent to or along a furrow containing plants.

When applied to the soil, the bait is applied at a rate corresponding to about 400 grams of active insecticidal ingredient per acre or less. Preferably, the baits are applied in the same manner as the conventional practice of banding at a rate within the range from about 100 to about 200 grams of active diabroticidal insecticide per acre. Immature beetles will feed on the cucurbitacin and, due to the structure of the bait, consume or contact a lethal quantity of the associated insecticide.

EXAMPLES

Examples 1–6

Samples having the proportions in Table 1 were prepared by dissolving the gelatin, carrageenan gum, sorbitol, sodium benzoate, and any food starch in water at 82° C. (180° F.). The solution was cooled to 60° C. (140° F.) and maintained at a pH of 5–6. Thereafter, carbaryl and ground root powder were dispersed and mixed until homogeneous. Thereafter, the materials were spray dried to form microspheroidal particles having a particle size between about 50 $\mu$m and 100 $\mu$m. The inlet temperature of the spray drier was 180° C., and the outlet temperature was 90° C. The spray had a flow rate of 10 g/minute at a pressure of 25 psig.

The samples were tested in a conventional laboratory bioassay test. The bait was suspended in corn oil and sprayed on the upper surfaces of test corn plants. Table 1 lists the average number of dead beetles found on each plant after an exposure of 18 hrs. to an environment containing 15 diabroticine beetles. Sample 2 is, however, an aged sample that was 24 hrs old before application and exposed on the plant for 20 hrs. Each sample was replicated 3 times. The results are an average of those replications.

TABLE 1

| Material (in % of total weight) | 1 | 2 (sample aged 24 hrs) | 3 | 4 | 5 | 6 |
|---|---|---|---|---|---|---|
| Gelatin (pork source) | 15.5 | 15.5 | 15 | 20 | 22.2 | 16.7 |
| Sorbitol | 5.2 | 5.2 | | 5 | 11.1 | |
| Modified food starch | | | 10 | | | |
| Carrageenan | 1.6 | 1.6 | | | | |
| Sodium benzoate | 0.1 | 0.1 | 0.1 | 0.1 | 0.1 | 0.1 |
| Buffalo Gourd Root Powder | 64.7 | 64.7 | 62.4 | 62.4 | 55.5 | 69.3 |
| Carbaryl | 10.3 | 10.3 | 10.0 | 10.0 | 8.9 | 11.1 |
| Avg. Dead | 14.3 | 13 | 12.7 | 12.3 | 12 | 12 |
| % Mortality | 96 | 87 | 84 | 82 | 80 | 80 |

Examples 1–6 illustrate the increase in mortality rates with an increase in cucurbitacin content (Examples 1, 4, and 5) and the effect of differences in formulation on beetle acceptance.

As a comparative example, buffalo gourd root powder and carbaryl ground to a size of 10–20 μm were suspended in corn oil and tested in parallel with examples 1–6. The mortality rate of the suspended particles was 98% (avg. dead was 14.7) after an exposure of 18 hours. The formulation was unstable, however, and separated into a thick paste of particles at the bottom of the corn oil. Such separation properties would dramatically increase the difficulties associated with shipping and storing a commercial product. Moreover, the corn oil suspension exhibited an efficacy period of only about 3 days even under dry conditions. The microspheres did not have the separation problems of the fine particles and exhibited an efficacy period of up to about 14 days under the same conditions.

Example 7

Example 7 is a modified version of example 1. The bait of example 7 contained the materials listed in Table 2 and exhibited a particle size of 50–100 μm.

TABLE 2

| Component | Weight % of total | Weight (mg/g microsphere) |
|---|---|---|
| Gelatin (pork source)[1] | 13.3 | 133 |
| Sorbitol | 4.5 | 45 |
| Carrageenan[2] | 1.4 | 14 |
| Sodium benzoate | 0.1 | 1 |

TABLE 2-continued

| Component | Weight % of total | Weight (mg/g microsphere) |
|---|---|---|
| Carbaryl[3] | 16.1 | 161 |
| Buffalo Gourd Root Powder | 64.7 | 647 |

[1]710 Dee-Gee Gelatin
[2]Gelcarin GP 812
[3]Carbaryl 80-W containing 80% active material The bait of example 7 was applied to test fields of corn in Nebraska. From each field, 48–96 plants were sampled. All fields had pretreatment counts of western corn rootworm beetles which were above the economic threshold for treatment. At the time of treating, 10% of the females were gravid, and the crop was in early milk stage.

The fields were treated by dispersing the bait in water and aerially broadcast in 40 foot swaths at a rate of 0.75 lb. microspheres per acre. This application rate translates into 0.1 lb. active carbaryl per acre. Striped plots were treated by interspersing a treated swath with an untreated swath. Therefore, the striped plots received half of the regular application rate, i.e., the striped plots received 0.375 lb/acre microspheres (0.05 lb/acre active carbaryl). Table 3 lists the conditions for each field.

TABLE 3

| Field No. | No. of Acres | Irrigated or Dry | Broadcast or Strip | Application Date |
|---|---|---|---|---|
| 1 | 10 | D | — | Untreated control |
| 2 | 12 | D | — | Untreated control |
| 3 | 56 | D | B | 8/2 |
| 4 | 15 | D | B | 8/1 |
| 5 | 30 | D | S | 8/1 |
| 6 | 12 | D | S | 8/1 |
| 7 | 15 | I | — | Untreated control |
| 8 | 125 | I | S | 8/1 |
| 9 | 40 | I | B | 8/2 |

Tables 4 and 5 report the results of monitoring the western corn rootworm (W), northern corn rootworm (N), and ladybug adults and larvae (L) in terms of the average number of beetles per plant. The ladybug count is used as a measure of the effects of the toxicant on beneficial insects. Low levels of impact on beneficials is, of course, desirable. It should be noted that only the western corn rootworm counts were at a level considered to be economically justified in treating.

TABLE 4

| | 7/26 (Before treatment) | | | 7/30 (Before Treatment) | | | 8/1 . . . 3–6 hrs After Treatment | | | 8/1 . . . 24 hrs After Treatment | | |
|---|---|---|---|---|---|---|---|---|---|---|---|---|
| Field | W | N | L | W | N | L | W | N | L | W | N | L |
| 1 | 1.9 | 0.9 | 0.5 | 1.6 | 0.3 | 0.2 | — | — | — | 1.8 | 0.8 | 0.2 |
| 2 | 2.0 | 0.06 | 0.19 | 2.3 | 0.17 | 0.25 | — | — | — | 1.8 | 0.33 | 0.37 |
| 3 | 2.4 | 0.9 | 0.5 | 2.3 | 0.4 | 0.8 | 0.1 | 0.1 | 0.1 | 0.1 | 0.08 | 0.2 |
| 4 | 2.7 | 0.7 | 0.1 | 2.3 | 0.6 | 0.2 | — | — | — | 0.17 | 0.4 | 0.1 |
| 5 | 1.6 | 0.4 | 0.7 | 2.2 | 0.6 | 0.7 | — | — | — | 0.1 | 0.08 | 0.14 |
| 6 | 2.5 | 0.6 | 0.35 | 1.9 | 1.0 | 0.11 | — | — | — | 0.09 | 0.21 | 0.03 |
| 7 | — | — | — | 3.06 | 0.88 | 0.19 | — | — | — | 2.0 | 0.8 | 0.19 |
| 8 | 1.9 | 0.08 | 0.25 | 1.9 | 0.36 | 0.2 | — | — | — | 0.26 | 0.21 | 0.14 |
| 9 | 1.6 | 1.8 | 0.08 | 1.5 | 0.7 | 0.17 | 0.08 | 0.17 | 0.06 | 0.14 | 0.12 | 0.2 |

TABLE 5

| Field | 8/6 (5 days after treatment) | | | 8/9 | | | 8/14 | | | 8/21 | | |
|---|---|---|---|---|---|---|---|---|---|---|---|---|
| | W | N | L | W | N | L | W | N | L | W | N | L |
| 1 | 1.1 | 0.25 | 0.08 | 0.9 | 0.6 | 0.2 | 0.35 | 0.12 | 0.15 | 0.16 | 0.04 | 0.19 |
| 2 | 1.35 | 0.17 | 0.25 | 1.1 | 0.23 | 0.14 | 0.6 | 0.2 | 0.14 | 0.1 | 0 | 0.08 |
| 3 | 0.1 | 0.08 | 0.1 | 0.08 | 0 | 0.1 | 0.08 | 0.04 | 0.2 | 0.04 | 0.02 | 0.08 |
| 4 | 0.06 | 0.04 | 0.14 | 0.08 | 0.06 | 0.06 | 0.06 | 0.04 | 0.3 | 0 | 0.02 | 0.06 |
| 5 | 0.08 | 0.07 | 0.14 | 0.09 | 0.07 | 0.14 | 0 | 0 | 0.12 | 0.02 | 0 | 0.12 |
| 6 | 0.05 | 0.06 | 0.13 | 0.08 | 0.05 | 0.15 | 0 | 0 | 0.08 | 0 | 0 | 0.08 |
| 7 | 1.7 | 0.37 | 0.23 | 2.4 | 0.6 | 0.46 | 1.6 | 0.6 | 0.2 | 0.02 | 0 | 0.08 |
| 8 | 0.05 | 0.05 | 0.2 | 0.13 | 0.08 | 0.16 | 0.02 | 0 | 0.08 | 0 | 0 | 0.02 |
| 9 | 0.1 | 0.02 | 0.23 | 0.17 | 0.04 | 0.17 | 0.02 | 0.04 | 0.19 | 0.02 | 0.02 | 0.02 |

Table 6 summarizes the western corn rootworm data from Tables 4 and 5 in conventional terms of an acreage-weighted average of mean plant beetle counts relative to the same field counts on 7/30 before treatment. The untreated control fields were contiguous to the treated fields and are used to gauge the local beetle population and the date when effects other than treatment begin to exert a dominating effect. From this average, the impact or control afforded by the invention is readily discerned.

TABLE 6

Western Corn Rootworm Summary

| Treatment | 7/30 Pre-treatment | 8/1 (3 hr) | 8/1 (24 hr) | 8/6 | 8/9 | 8/14 | 8/21 |
|---|---|---|---|---|---|---|---|
| Dry control | 1.98 | — | 1.8 | 1.23 | 1.0 | 0.49 | 0.13 |
| % of Pre-treatment | 100 | — | 91 | 62 | 51 | 25 | 6.6 |
| Dry Treated | 2.2 | 0.1 | 0.11 | 0.08 | 0.08 | 0.05 | 0.02 |
| % of Pre-treatment | 100 | 4.5 | 5.0 | 3.6 | 3.6 | 2.3 | 0.9 |
| Irrigated Control | 3.06 | — | 2 | 1.7 | 2.4 | 16 | 0.02 |
| % of Pre-treatment | 100 | — | 65 | 56 | 78 | 52 | 0.6 |
| Irrigated Treated | 1.8 | 0.08 | 0.2 | 0.06 | 0.14 | 0.02 | 0.005 |
| % of Pre-treatment | 100 | 5.3 | 11 | 3.3 | 7.7 | 1.1 | 0.2 |

Figure 1:
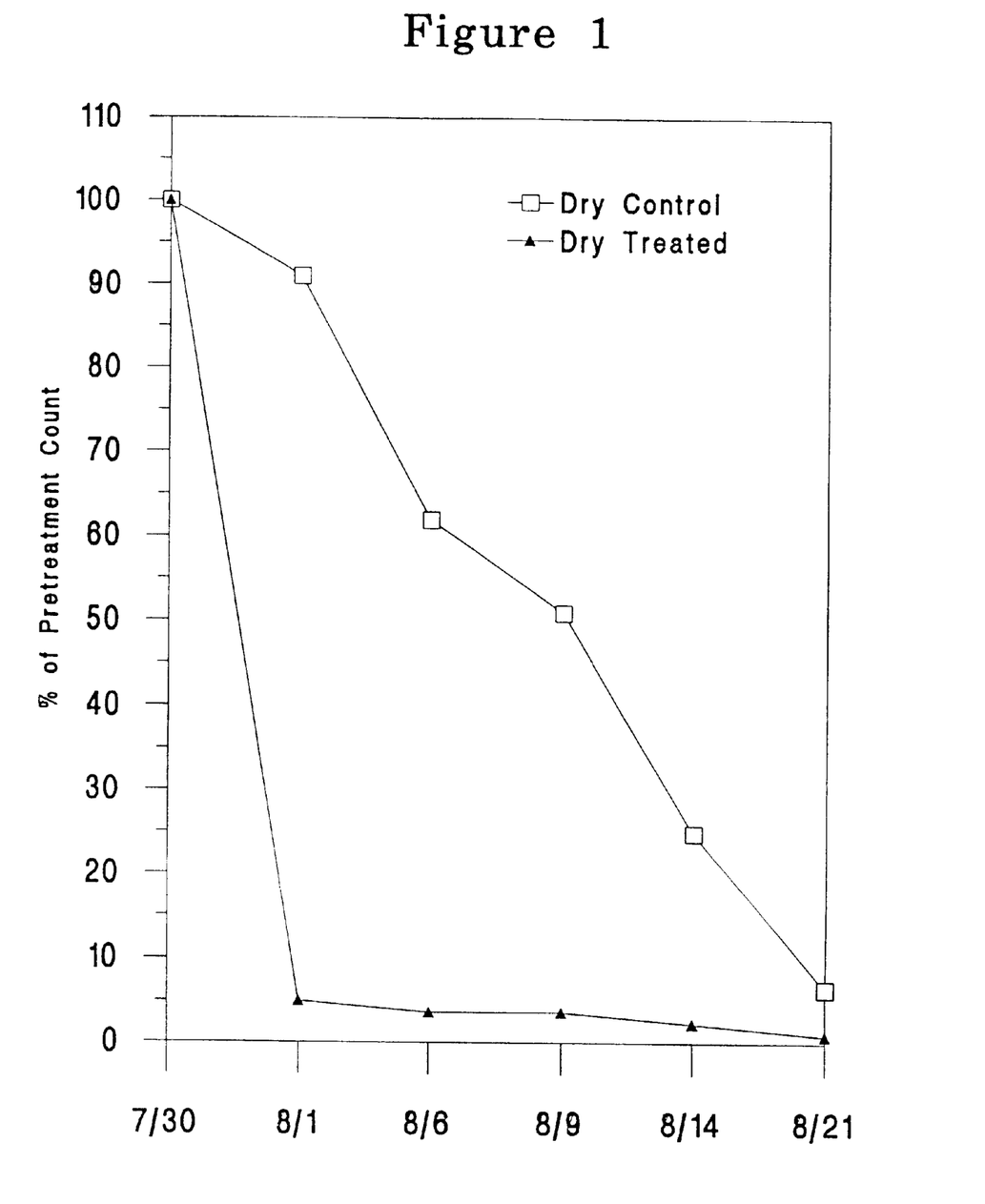
FIG. 1 is a graph showing the control afforded by the present invention over western corn rootworm in dry fields.
Figure 2:
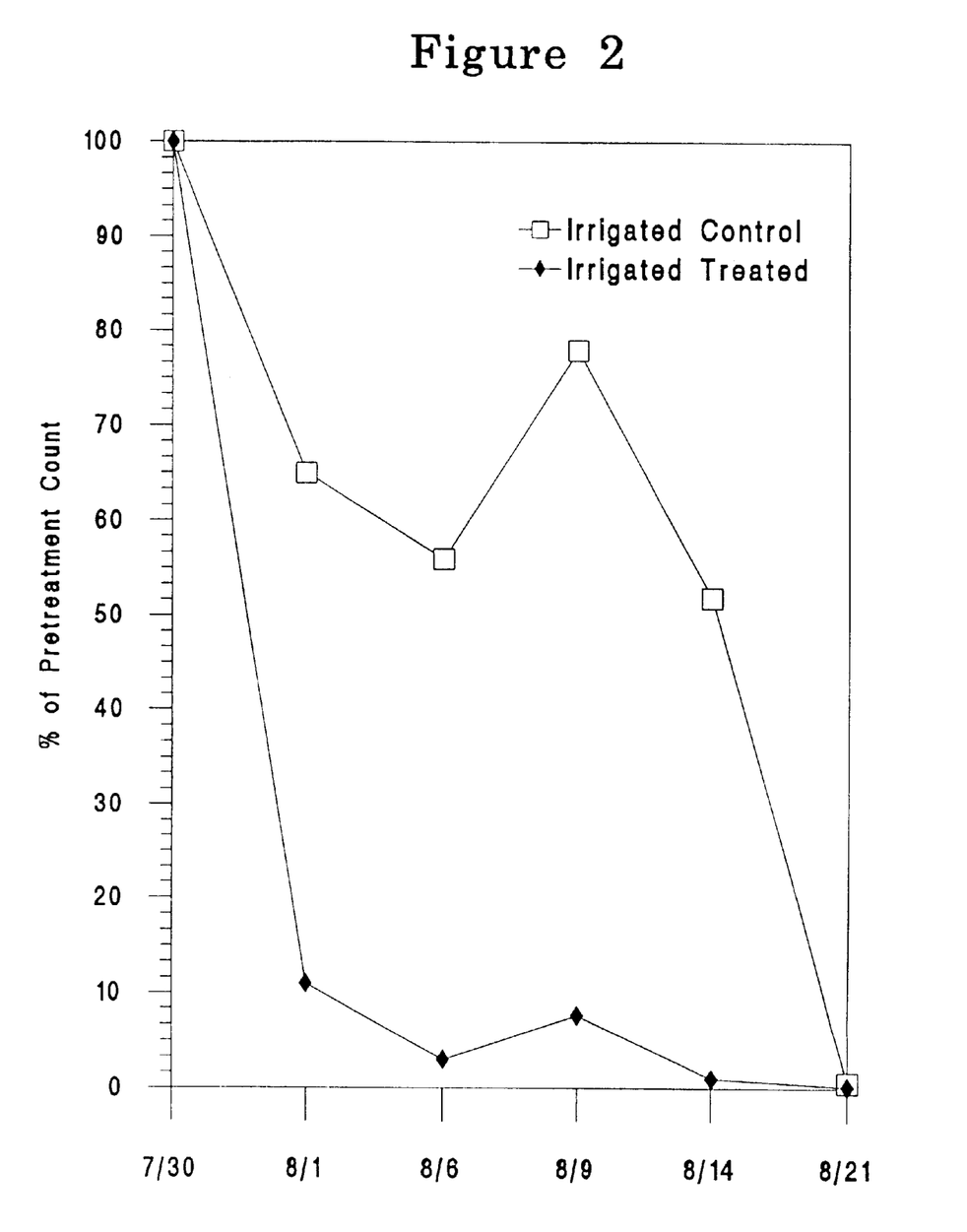
FIG. 2 is a graph showing the control afforded by the present invention over western corn rootworm in irrigated fields.
Figure 3:
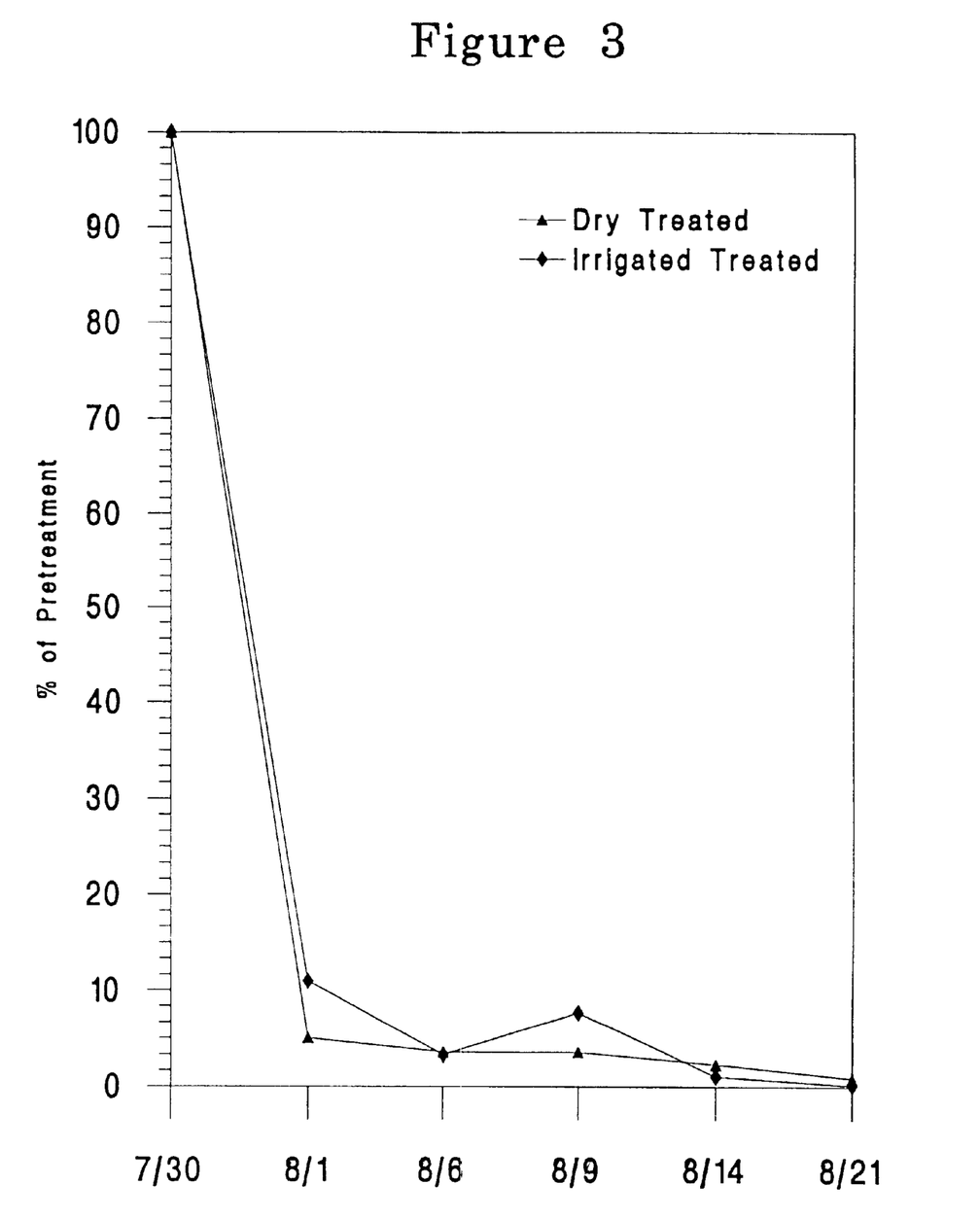
FIG. 3 is a graph showing the control afforded by the present invention over western corn rootworm in dry v. irrigated fields.

The information from Table 6 is graphically presented in FIGS. 1–3. FIG. 1 shows the mean beetle counts of the dry control plants and the plants treated with baits according to the invention without irrigation over a 3 week period. FIG. 2 shows the same type of comparison but in fields that were irrigated by conventional irrigation methods. FIG. 3 compares the dry beetle counts against the irrigated field counts.

As seen from the high levels of control under actual field conditions, bait according to the present invention provides good control over corn rootworm population.

Example 8

In example 8, microspheres from example 1 were aerially applied at a rate corresponding to 0.75 lbs of microspheres (340 g) per acre to two fields (150 acres and 130 acres) exhibiting an infestation of northern corn rootworm. As above, the untreated control field was contiguous and used to monitor area beetle population changes. Table 7 reports the acreage-weighted average beetle count of the test fields and the control field.

TABLE 7

Northern Corn Rootworm Tests

| Treatment | 8/9 (Pretreatment) | 8/13 (4 days) | 8/20 (11 days) | 8/27 (18 days) |
|---|---|---|---|---|
| Control | 1.5 | 3.5 | 1.3 | 0.8 |
| % of Pretreatment | 100 | 233 | 87 | 53 |
| Treated Fields | 1.7 | 0.2 | 0.1 | 0.1 |
| % of Pretreatment | 100 | 12 | 6 | 6 |

As an examination of table 7 shows, the area beetle population increased by more than twice in the 4 days after treatment. Notwithstanding this increase, baits according to the present invention continued to provide good population control through this increased population period and for the succeeding two weeks.

Examples 9–14

In examples 9–14, bait formulations according to the invention were prepared and tested for efficacy as a soil bait against immature corn rootworm beetles (larvae). All baits had the basic formulation shown in Table 8. Milled corn germ containing less than 25 wt % associated corn endosperm was added as an auxiliary feeding stimulant.

TABLE 8

| Component | % by Weight |
|---|---|
| Carrageenan gum | 3 |
| 300 Bloom Type A gelatin | 7 |
| Sorbitol plasticizer | 6 |
| Sodium benzoate preservative | 0.1 |
| Cucurbitacin liquid[1] | 10 |
| Corn germ (milled) | 40.6 |

[1]Fresh Liquor containing 40 wt % solids (100 g liquor = 2000 ppm Cucurbitacin E) from concentration of zucchini fruits high in cucurbitacin content.

The specific toxicant for each bait formulation is listed in Table 9. The amount of added clay was adjusted to compensate for differences in the amount and density of toxicant. The amount of clay within the tested amounts was not expected to significantly affect palatability of the bait to the test larvae.

TABLE 9

| Example | Clay (wt %) | Toxicant | Weight % |
|---|---|---|---|
| 9 | 23.3 | Carbaryl | 10 |
| 10 | 28.3 | Carbaryl | 5 |
| 11 | 28.3 | Chlorpyrifos | 5 |
| 12 | 30.8 | Chlorpyrifos | 2.5 |
| 13 | 29.3 | Phorate | 4 |
| 14 | 31.3 | Phorate | 2 |

Each bait formulation was tested for efficacy by mixing the bait into soil surrounding the roots of living corn plants. Each test was replicated twelve times. An equal number of corn rootworm larvae were introduced into each sample plot. The number of live larvae found in the soil and near the roots was counted at one, four, and six weeks after introduction. Control at the six week period is a measure of the bait's ability to withstand microbial attack. Table 10 reports the results.

TABLE 10

| | Number of Live CRW Larvae (avg.) | | | | | | | | |
|---|---|---|---|---|---|---|---|---|---|
| | 1 week | | | 4 weeks | | | 6 weeks | | |
| Example | Soil | Roots | Total | Soil | Roots | Total | Soil | Roots | Total |
| Control | 30 | 3 | 33 | 13 | 5 | 18 | 9 | 1 | 10 |
| 9 | 26.7 | 8 | 34.7 | 1.7 | 0 | 1.7 | 6.7 | 1.7 | 8.3 |
| 10 | 17 | 6.3 | 23.3 | 2 | 0 | 2 | 1 | 1.7 | 2.7 |
| 11 | 2.3 | 0.7 | 3 | 0 | 0 | 0 | 0.3 | 0.3 | 0.7 |
| 12 | 1 | 0 | 1 | 0 | 0 | 0 | 0 | 0 | 0 |
| 13 | 1.7 | 0 | 1.7 | 0.3 | 0 | 0.3 | 0 | 0.3 | 0.3 |
| 14 | 5 | 0.3 | 5.3 | 0.3 | 0 | 0.3 | 0 | 0 | 0 |

The examples presented herein are intended to serve as an aid to understanding the present invention. Specific materials and particle sizes exemplified are not intended to serve as a limitation on the scope of the appended claims.

What is claimed is:

1. A particulate bait composition useful for controlling insect populations, said composition comprising, based on total weight of said bait: 0.01–99 wt % of an insecticide and 0.01–99 wt % of a feeding stimulant comprising a cucurbitacin homogeneously distributed throughout a binder which comprises gelatin.

2. A bait composition as in claim 1 wherein said insecticide is selected from the group consisting of organophosphates, carbamates, bacillus thuringiensis, and diabroticidal viruses.

3. A bait composition according to claim 1 wherein said insecticide is selected from the group consisting of phorate, chlorpyrifos, and carbaryl.

4. A bait as in claim 1 wherein said binder further comprises a plasticizer and a preservative.

5. A bait as in claim 1 wherein said binder comprises gelatin having a bloom strength within the range from about 200–300.

6. A bait as in claim 1 wherein said bait exhibits the form of a dry granular bait.

7. A bait as in claim 1 wherein said cucurbitacin has been added to the gelatin binder as a concentrated liquid containing more than 0.01 wt % cucurbitacins and homogeneously dispersed throughout the gelatin binder.

8. A bait as in claim 1 wherein said cucurbitacin has been added to the gelatin binder as a concentrated liquid containing more than 0.1 wt % cucurbitacins and homogeneously dispersed throughout the gelatin binder.

9. A method for controlling insect populations on plants consumed by said insects, said process comprising:

applying to an area exhibiting infestation by an insect that feeds on cucurbitacin-containing plant tissues an amount of a particulate bait according to claim 1 in an amount that is effective to kill at least a portion of the immature or adult insects in said area.

10. A method according to claim 9 wherein the applying step comprises applying said bait to soil.

11. A method according to claim 9 wherein the applying step comprises applying said bait to plant foliage.

* * * * *